(12) United States Patent
Kenney et al.

(10) Patent No.: US 8,187,868 B2
(45) Date of Patent: *May 29, 2012

(54) DEVICE FOR TRAPPING EXTRANEOUS GAS

(75) Inventors: David A. Kenney, Lunenburg, MA (US); Joseph C. Wall, Southborough, MA (US); Todd M. Upton, Eliot, ME (US); Henry J. Cattadoras, Old Orchard Beach, ME (US); Gregory R. Martin, Acton, ME (US); Allison J. Tanner, Portsmouth, NH (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/686,007

(22) Filed: Jan. 12, 2010

(65) Prior Publication Data

US 2010/0112698 A1    May 6, 2010

(51) Int. Cl.
*C12M 1/24*    (2006.01)

(52) U.S. Cl. ............... 435/294.1; 435/299.2; 435/304.1; 435/304.2

(58) Field of Classification Search .................. None
See application file for complete search history.

(56) References Cited

U.S. PATENT DOCUMENTS

| 3,682,088 | A | 8/1972 | Paniez | 99/277.2 |
| 5,122,267 | A | 6/1992 | Giovanetti et al. | 210/188 |
| 5,704,504 | A | 1/1998 | Bueno | 215/381 |
| 6,260,474 | B1 | 7/2001 | Yahav | 99/277.1 |
| 2007/0166822 | A1 | 7/2007 | Kenney et al. | 435/325 |

FOREIGN PATENT DOCUMENTS

WO    2008/106012    9/2008

*Primary Examiner* — Jim Ketter
(74) *Attorney, Agent, or Firm* — Susan S. Wilks (57) ABSTRACT

A device for trapping extraneous gas or bubbles is disclosed. The device is defined as having a gas collection area in a tapered neck portion such that when used as a cell culturing apparatus, extraneous gas or bubbles are trapped and isolated from the cell growth areas where cells or media reside.

13 Claims, 7 Drawing Sheets

DEVICE FOR TRAPPING EXTRANEOUS GAS

CROSS-REFERENCE TO RELATED APPLICATIONS

This application is a continuation of Application Ser. No. 11/454,964, filed Jun. 15, 2006, which claims the benefit of U.S. Application Ser. No. 60/755,809 filed on Dec. 30, 2005 and entitled "Device for Trapping Extraneous Gas" which is incorporated by reference herein.

FIELD OF THE INVENTION

The present invention relates generally to a device for trapping extraneous gas and, in particular, to a bubble trap for a cell cultivating flask.

BACKGROUND OF THE INVENTION

In vitro culturing of cells provides material necessary for research in pharmacology, physiology, and toxicology. The environmental conditions created for cultured cells should resemble as closely as possible the conditions experienced by the cells in vivo. An exemplary flask inclusive of a suitable environment for culturing cells is a common laboratory flask. The cells attach to and grow on the bottom surface(s) of the flask, immersed in a suitable sustaining media. With the advent of cell-based high throughput applications, cell culture vessels have been developed to provide an increased surface area for cell growth while also providing necessary gas exchange. These systems employ traditional cell culture vessels including common flasks, roller bottles, cell culture dishes, and multi-layered cell growth vessels. In addition, automation permits manipulation of the cell culture vessel much like that performed by the manual operator.

Even further, flask volumes having multiple layers of cell growth are capable of producing a greater cell yield than commonly known flasks that permit growth of cells on a single bottom wall. The multiple layers may permit gas exchange at a surface of cell attachment or an alternate surface, therefore alleviating the need for head space above the cell growth media. In some flasks, particularly those with multiple layers and/or flasks designed to be completely filled with media, the presence of any air or gas above the liquid media is detrimental to cell growth within the tracheal flask. In particular, a bubble or gaseous material above the media or cells prevents the cells from obtaining necessary nutrients for cellular growth. In addition, the bubble occupies the space between the layers restricting gaseous exchange and the equilibration of gases (e.g., $O_2$ and $CO_2$) between the cells or media and external environment.

In addition, when a flask is vertical filled with media, residual air remains at the top. However, tilting of the flask on its side (permitting adhesive/attachment-dependent cells to grow on internal surfaces) can allow the residual air to make its way in between the surface layers for cell culture, further impeding cellular growth. Alternatively, overfilling the flask would help to eliminate air/gas bubbles, but would also cause contamination.

There is a need for a cell culture flask that can provide an increased surface area for cell growth while preventing residual air/gaseous material from entering the regions of cellular growth. Additionally, the confinement of extraneous gaseous material in a region of the flask away from cellular growth would permit sufficient exchange of nutrients between the media and the multitude of attachment-dependent cells. It would be beneficial to prevent air or gas bubbles that remain in a top portion of a vessel from entering the areas of cell growth during manipulation of the flask from a vertical filling position to a horizontal cell growth position. Consequently, the desired cell culture flask may also be suitable for use in the performance of high throughput assay applications that commonly employ robotic manipulation.

SUMMARY OF THE INVENTION

According to an illustrative embodiment of the present invention, a device for efficient culturing of cells is disclosed. The illustrative device for trapping extraneous gas or bubbles comprises one or more surfaces defining an internal volume, at least one opening in a surface, and a gas collection area incorporated within the internal volume such that when the internal volume is substantially filled with a liquid or aqueous mixture, and tilted, the gas collection area traps the extraneous gas or bubbles.

In another aspect of the device of the present invention, a cell growth apparatus for trapping extraneous gas comprises one or more surfaces defining an internal volume, at least one opening in the one or more surfaces, and a gas collection area incorporated within the internal volume whereby when the internal volume is substantially filled with a liquid and tilted, the gas collection area traps extraneous gas or bubbles.

In addition, a method of culturing cells using the cell growth apparatus of the present invention comprises steps of: providing a cell growth apparatus of the present invention, introducing cells and/or media into said cell growth apparatus in a vertical filling position, filling the internal volume substantially to a level below the opening, closing the opening, positioning or tilting the apparatus to a horizontal cell growth position, allowing extraneous gas or bubble(s) to be captured in a gas collection area of the apparatus, and then incubating the apparatus.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion.

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Figure 1A:
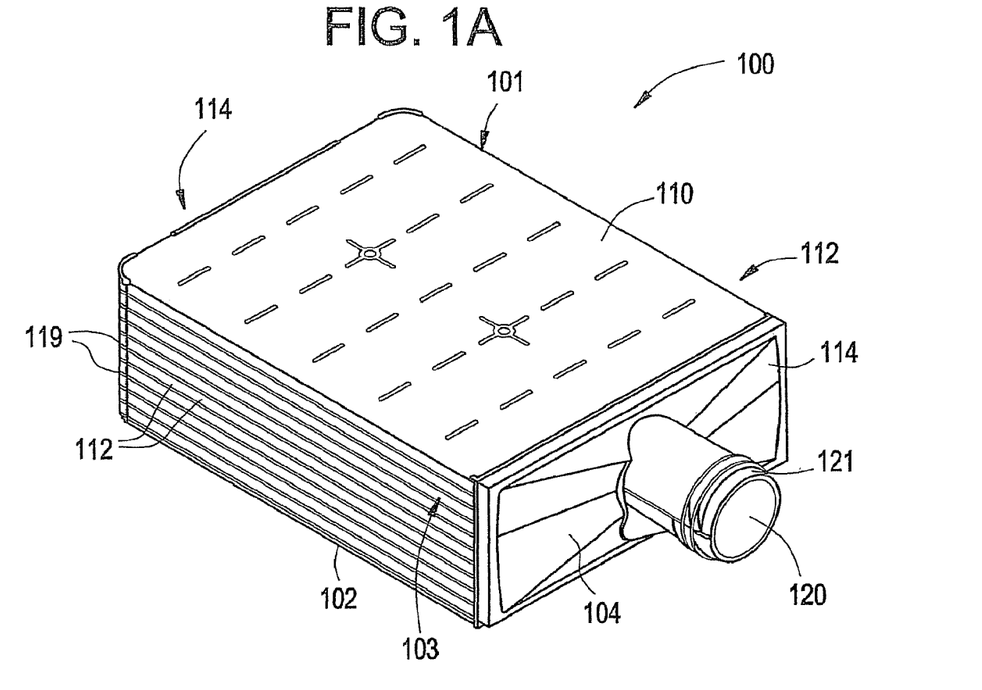
FIG. 1A is a perspective view of a flask.
Figure 1B:
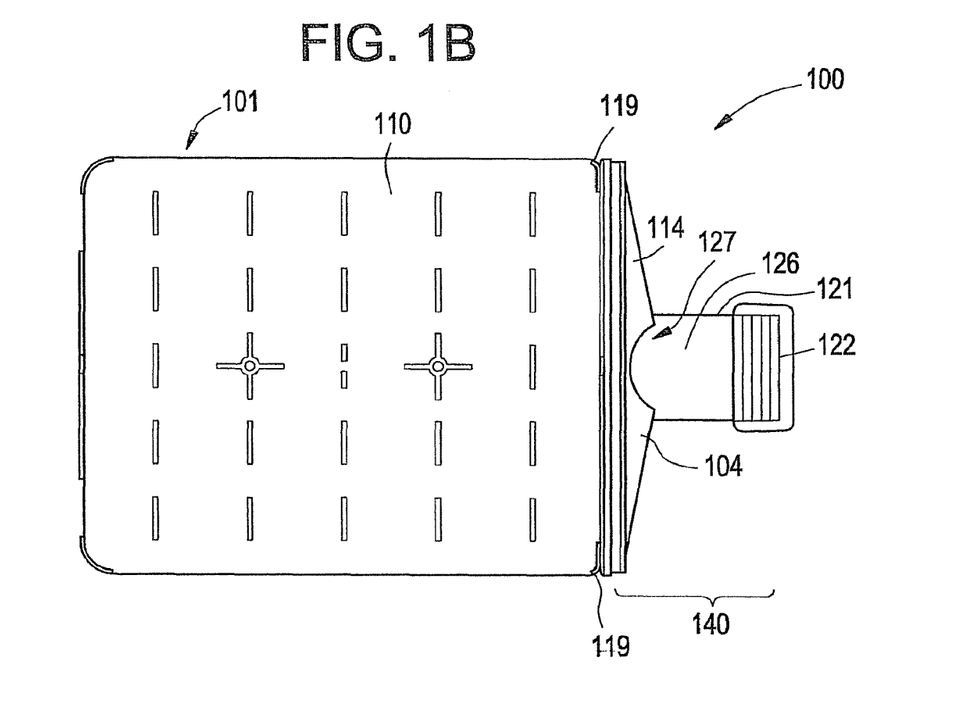
FIG. 1B is an external top view of a flask.
Figure 1C:
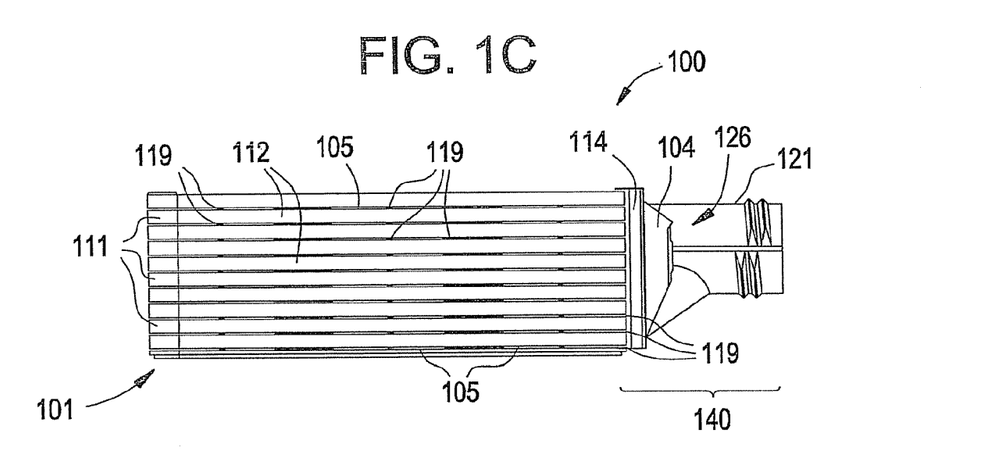
FIG. 1C is an external perspective side view of a cell growth flask.
Figure 1D:
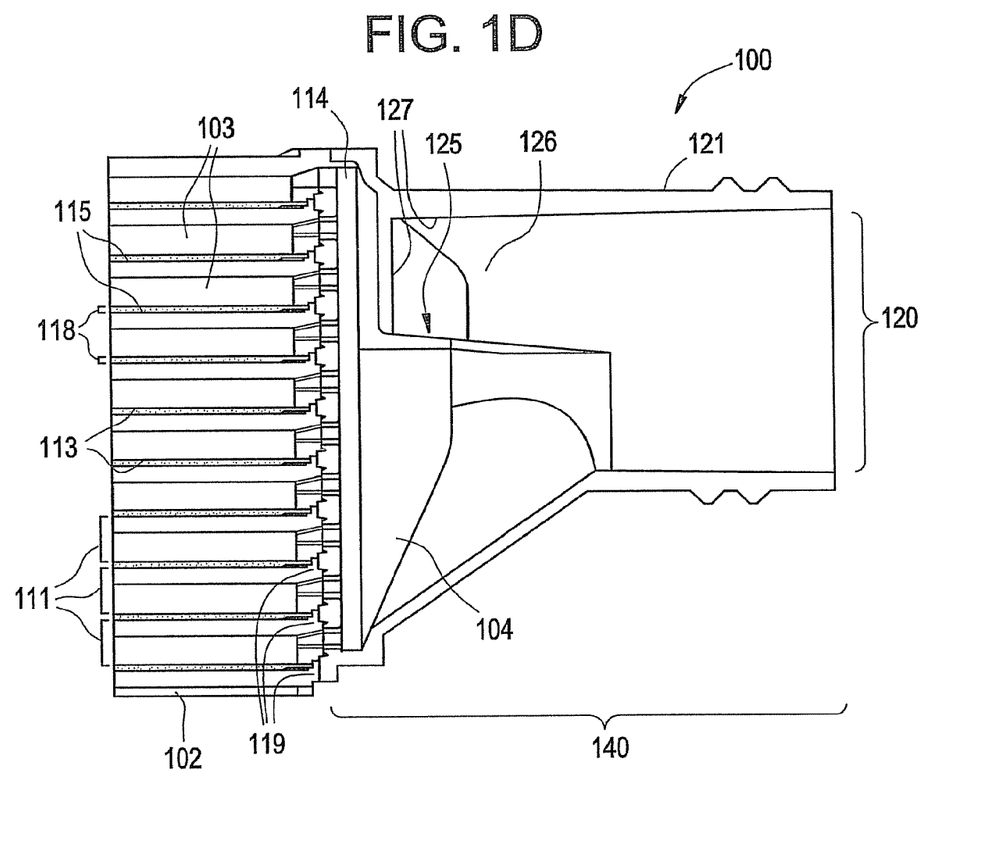
FIG. 1D is a partial cross-sectional perspective side view of an embodiment of the present invention.

In accordance with one embodiment of the present invention, an external view of a device is shown in FIG. 1A-1D. The cell growth apparatus 100 of this embodiment takes the form of a flask 100; the flask 100 comprises an outer vessel body 101 (see FIG. 1A/1B) defined by a top plate 110, a bottom tray 102, sidewalls 112, and end walls 114, further defining an internal volume 103. Disposed within the flask is a bubble trap or flange 125 that prevents air, gas or bubbles from entering the internal volume 103. The flange 125 is designed so that it does not occupy the entire opening 120 to the internal volume 103 of the apparatus 100. As illustrated in this embodiment, the flange 125 is a projection in a tapered neck portion 140 of the flask 100 extending from an interior surface or perimeter 127 in FIG. 1B of the opening 120. The flange 125 forms a gas collection area 126 in a tapered neck portion 140 of the flask 100 which serves to trap bubbles or extraneous air/gas when the flask is moved from a vertical position (with opening 120 facing upward) to a horizontal position (with top plate 110 facing up). In one embodiment, a plurality of individual cell growth chambers 111 are preferably disposed within the internal volume 103 the flask (FIG. 1C). The individual cell growth chambers 111 are each defined by a generally transparent bottom surface 113 and a generally transparent top surface 115. The surfaces 113 and 115 are attached to the flask body 101 along the sidewalls 112 and end walls 114. Preferably, the bottom surfaces 113 within each chamber 111 are made from gas permeable, liquid impermeable material that is capable of supporting cell growth. Each top surface 115 is preferably a rigid, generally gas impermeable material (preferably transparent) that will provide support to the cell growth chamber 111. In this embodiment, a gas permeable surface 113 is adhered in a leak-proof sealing to the flask body 101 by using supports 119. Supports 119 extend from the flask body 101 and provide structural support to the surface/membrane 113. Tracheal spaces 118, or tracheal chambers 118, are created between each cell growth chamber 111 (FIG. 1C/1D). The opposing top surface 115 of each chamber 111 defines an upper wall to the cell growth chamber 111 as well as a bottom portion of a tracheal chamber 118. Each cell growth chamber 111 therefore alternates with a tracheal chamber 118 in vertical successive orientation. Portals 105 allow air to circulate through the tracheal chambers 118 for gas exchange with the external environment and the internal volume 103 via the gas permeable surfaces 113. The gas collection area 126, however, is internally located within the tapered neck portion 140 and isolated away from the cellular growth chambers 111 (to trap any gaseous fractions, air or bubbles, that remain in the flask subsequent filling the flask with media and/or cells). Accessibility to the cellular growth chambers 111 is achieved via an aperture 120 within the flask body 101. The aperture 120 has a neck 121 and is connected to the cell growth chambers 111 via a manifold 104 in FIG. 1D. The manifold 104 is a portal providing access to the internal volume 103. The trap/flange 125 acts as a physical barrier 125 preventing any air/gas that remains in the neck 121 after the flask is filled with media, and capped, from migrating into the cell growth region of the flask as it is positioned from the vertical filling position [with the opening facing upward (FIG. 2A)] to the horizontal cell growth position [with the bottom tray 102 contacting an external planar surface and the top plate 110 facing upright (FIGS. 1A-1D)].

The cell growth chambers, however, are not required. The device is useful in any instance where an absence of head space within a flask is required or preferred.

The apparatus 100 of the present invention may be made by any number of acceptable manufacturing methods well known to those of skill in the art. In a preferred method, the apparatus 100 is assembled from a collection of separately injection molded parts. Although any polymer (such as polystyrene, polycarbonate, acrylic, polystyrene, or polyester) suitable for molding and commonly utilized in the manufacture of laboratory ware may be used, polystyrene is preferred. Preferably, the flange 125 is designed in such a way that it may be integrally molded with the top plate 110 and easily ejected from a mold. In another embodiment, the flange 125 is injection molded with the neck 121 which is included with the manifold 104. If manufactured separately, however, the flange 125 may be properly fixed to the interior surface of the flask body 101 by any number of methods including but not limited to: adhesive or solvent bonding, heat sealing or welding, compression, ultrasonic welding, laser welding and/or any other method commonly used for generating seals between parts such that it becomes an integral portion of the interior surface 127 of the apparatus. Once the flange 125 is adhered, then the top plate 110 and bottom tray 102 may be aligned and joined, such as by laser welding. Finally, when a cap 122 is provided, it may be a screw cap, snap-fit cap, cap with septum, cap with air holes, or any cap known in the art. In one embodiment, the cap 122 is positioned to access the contents of the apparatus 100 via an end wall 114. Alternatively, the cap 122 may be positioned with the top plate 110. Other accessibility options may include a neck and cap arrangement within a corner region of the apparatus 100, such that the cap 122 would not protrude from the periphery of the apparatus body 101. A straight or angled neck 121 may be employed based upon access or filling requirements. A septum included in a cap 122 allows a canula, tip or needle to access the contents of the apparatus 100 without the need for unscrewing the cap. The septum is leak-proof, puncturable and capable of resealing once the needle, tip or canula is removed from the apparatus, even after multiple punctures. Furthermore, a septum allows access to the extraneous gas or bubbles for removal.

In another embodiment (See FIG. 4), a cap 422 is utilized in which a flange 425 is integral with the cap 422 to facilitate removal of extraneous gas components or bubbles from a vessel 400. As such, the cap 422 has a flange or obstruction 425 that projects into the internal volume 403 so that following a step of filling the flask 400, the cap 422 is secured to the neck 440. The flange 425 which defines a gas collection area 426 is then employed when the flask 400 is tilted from a vertical filling position to a horizontal growth position (as shown).

A cap and neck arrangement is not necessary, however, for an apparatus of the present invention. As such, the bubble trap 125 can be incorporated as a wall or projection 125 in any a tapered neck portion 140 of an apparatus such that tilting of the apparatus allows gas and/or bubbles to remain isolated from the cell growth areas 111 in a gas collection area 126. Further, any means of access into the cell culture chamber(s) 111 may be employed as known by one skilled in the art.

Cell growth may be monitored from time to time by microscopic or visual inspection through the generally transparent interior and exterior surfaces of the apparatus 100. Easier accessibility and greater visibility of cellular growth can be visualized when optical lenses having varying magnifications are employed in the external body 101. Optical lenses provide confirmation that no extraneous gas or bubbles exist within the internal volume 103.

Figure 2A:
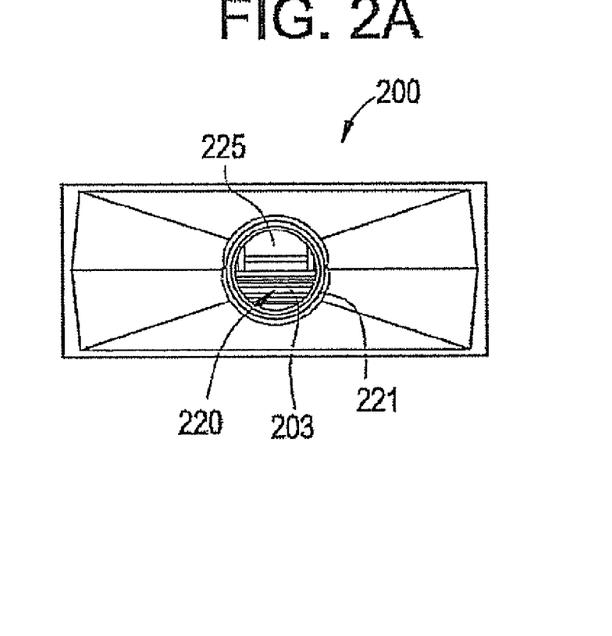
FIG. 2A is an external top view of a device in a vertical filling position in an embodiment of the present invention.

In use, the apparatus 100 of the current invention is employed according to accepted cell growth methods. Cells and/or media are introduced to the apparatus 100 though the aperture/opening 120 via the neck 121 (or through a septum in the opening 120) in a vertical filling position. The vertical filling position situates the apparatus 100 with the opening 120 upright (in an upward-facing direction) so that the apparatus 100 may be filled with cells and/or media as known by one of skill in the art. FIG. 2A is a perspective view looking into an apparatus 200 via the opening 220. The apparatus 200 is arranged such that the cell-containing media covers the cell growth surfaces of the internal volume 203. Advantageously, the apparatus 200 is capable of being completely filled with media, substantially filling the internal volume 203 to a level above the end 228 of the flange 225. Thus, the substantial filling of the internal volume with media minimizes the amount of trapped air above the flange 225. In one embodiment, the internal volume 203 is substantially filled to a level about half way or more up the neck 221 such that the flange 225 takes up ⅓ to ½ of the neck 221 and is still capable of trapping the amount of air remaining in the flask. Accordingly, the volume of air remaining in the apparatus 200 is preferably less than the volume of the gas collection area 226. The flask 200 is tilted to a horizontal growth position with the top plate 210 upright and the bottom tray 202 downward (as also illustrated in FIGS. 1A-1D where attachment/anchorage-dependent cells can grow on surfaces within the cell culture chambers 111). Tilting of the apparatus from the vertical filling position to the horizontal growth position also permits extraneous gas or bubbles within the liquid media to be captured and trapped in the gas collection area 226. (See an internal side view of the tapered neck portion 140 [240] in FIG. 1D [FIG. 2B] when the apparatus 100 [200] is in the horizontal growth position.) Trapping extraneous air and bubbles in the gas collection area 226 ensures the free flow and exchange of gases between the flask interior 203 and the external environment without inhibiting the growth of cells. Removal of the extraneous gas or bubbles from the gas collection area by way of a canula, syringe, or other instruments further prevents the gas/bubbles from inadvertently entering the liquid media or cell growth areas. The apparatus is then placed within an incubator such that the bottom tray 202 assumes a horizontal position and allows a number of cell cultures to be simultaneously grown when similar vessels are stacked together.

During the cell growth process, it may become necessary to extract the exhausted media and insert fresh media. The flange 125, or gas collection area 126, as previously described, does not occupy the entire opening 120 and does not interfere with media replacement via the capped opening or by insertion of a canula or syringe, for example, through the septum. Once the cells are ready for harvesting, a chemical additive such as trypsin is added to the apparatus through the septum without interference from the flange 125. Another advantage of the apparatus 100 of the present invention is its enhanced capacity to grow cells on an opposing surface when the apparatus is rotated about 180° such that the top plate 110 faces down. Thus, when the apparatus 100 is rotated, cells can be cultured on an alternate surface of a cell growth chamber 111.

Figure 8A:
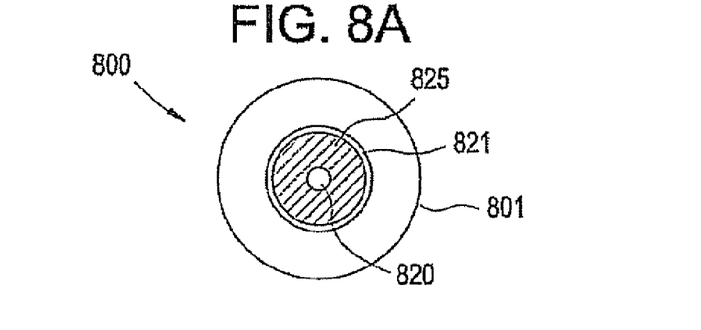
FIG. 8A is an external top view of a device in a vertical filling position in a further embodiment of the present invention.
Figure 8B:
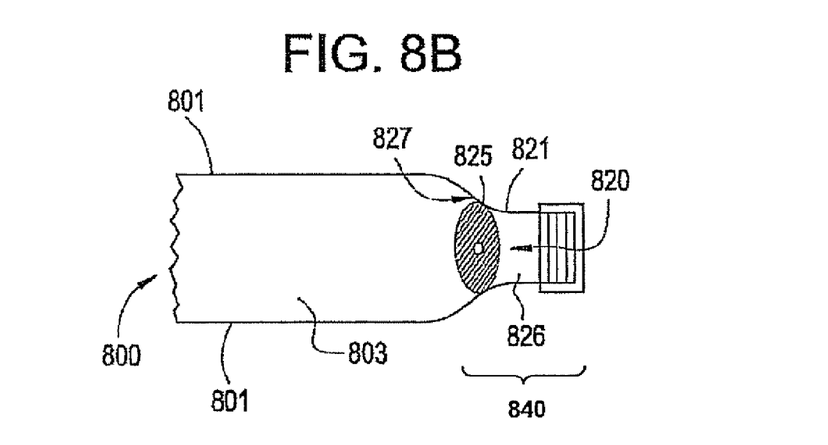
FIG. 8B is a cross-sectional side view of the further embodiment of FIG. 8A.

It is possible, however, to incorporate the flange 125 and/or gas collection area 126 in a variety of cell culturing vessels including roller bottles and stackable devices that may include recurring steps of rotating the apparatus (e.g. about 360°). In one embodiment, a round vessel 800 (FIGS. 8A & 8B) has a vessel body 801 in FIG. 8B that defines an internal volume 803 which includes a tapered neck portion 840. As illustrated, the tapered neck portion 840 has a circumferential flange 825 formed as a radial wall 825 extending from an inner peripheral surface 827 in FIG. 8B of the tapered neck portion 840 toward the internal volume 803. The radial wall 825 further extends toward an opening 820 that provides access to the internal volume 803. The radial wall 825 and the inner peripheral surface 827 of the neck 821 define a gas collection area 826. Any gas or bubbles remaining in the internal volume 803 or the tapered neck portion 840 are trapped in the gas collection area 826 when the vessel 800 is tilted from a vertical filling position with the opening 820 facing upward (See FIG. 8A) to a horizontal cell growth position (See FIG. 8B). The gas or bubbles reside in the gas collection area 826 isolated from the internal volume 803 as the vessel 800 rolls.

Embodiments of the present invention are for exemplary purposes only and not limitation. Other embodiments of an apparatus/vessel of the present invention may incorporate raised corners, posts, ledges, stand-offs or any other feature that will allow spacing between successively stacked flasks. The standoffs may be molded onto an exterior surface of the apparatus and may be cast at any angle, having any size or dimension to facilitate growth of cells away from extraneous gases/bubbles. The stand-offs further ensure lateral stability of the stacked vessels. The manifold is further capable of including a diversified arrangement of projections to trap extraneous gas or bubbles in multiple gas collection areas.

Figure 2B:
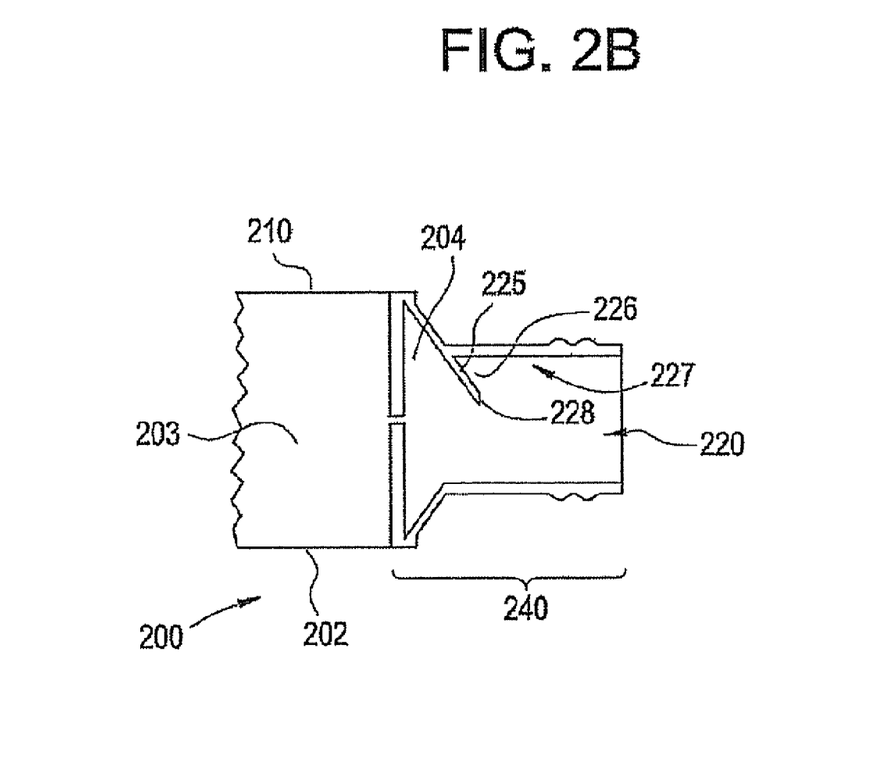
FIG. 2B is a cross-sectional side view of an embodiment of the present invention in a horizontal cell growth position.
Figure 3:
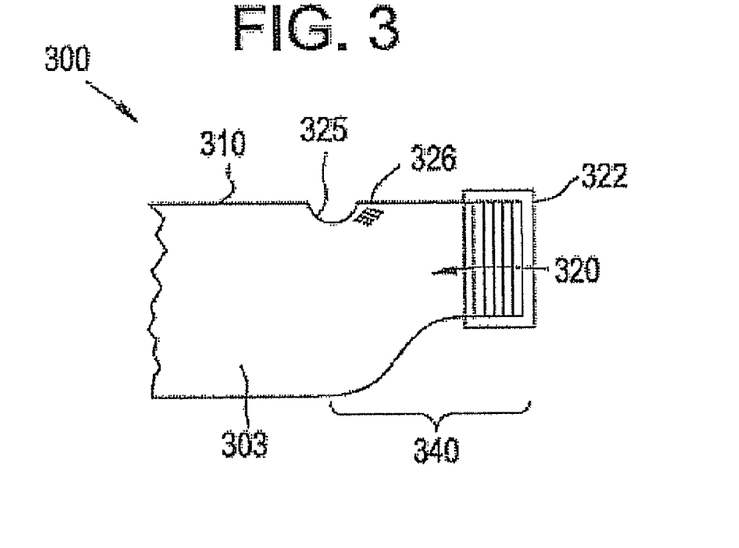
FIG. 3 is a partial cross-sectional side view of a further embodiment of the present invention.

Furthermore, the bubble trap or gas collection area 126 may be defined by any flange and/or wall of a vessel body or neck, or may be any format in the internal volume and/or any format in a surface of the internal volume 103. For instance, the flange 225 as shown in FIG. 2B may be angled at any gradation from the wall of the neck and take any size, shape, or form within the internal volume 103 or tapered neck portion 140. For exemplary purposes only, and not limitation, a U-shaped projection 325 as shown in FIG. 3 can be easily molded with a top plate 310 to define a gas collection area 326. The top plate 310 is upright in a horizontal position as seen in the cross-sectional side view of a vessel 300. When the vessel 300 is in a vertical position in which an opening 320 faces upright, the vessel 300 is filled with cells or media, or another liquid mixture. The opening 320 remains accessible through a removable cap 322. When the vessel 300 is tilted from a vertical filling position with the opening 320 facing upward to a horizontal growth position (as shown), the gas collection area 326 confines gas and/or bubbles in the tapered neck portion 340 and isolates the gas and/or bubbles from the liquid portion of the internal volume 303.

Figure 4:
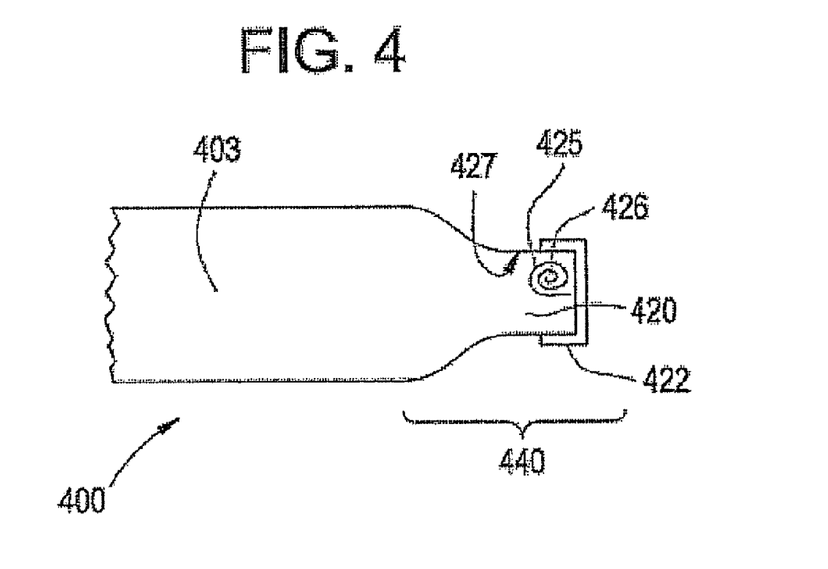
FIG. 4 is a partial cross-sectional side view of a further embodiment of the present invention.

Alternatively, a gas collection area 426 (FIG. 4) may be formed by a spiracle projection 425. The spiracle projection 425 is a flat structure protruding from a surface 427 of the vessel body 400 and spiraled such that any gas or bubbles remaining in the vessel is trapped within the gas collection area 426 of the spiral projection 425 when the opening 420 is tilted from a vertical upright position to the horizontal growth position (as seen in FIG. 4). For exemplary purposes only and not further limitation, the spiracle shaped flange 425 in this embodiment is incorporated with a removable cap 422 in forming a gas collection area 426 within a tapered neck portion 440.

Figure 5:
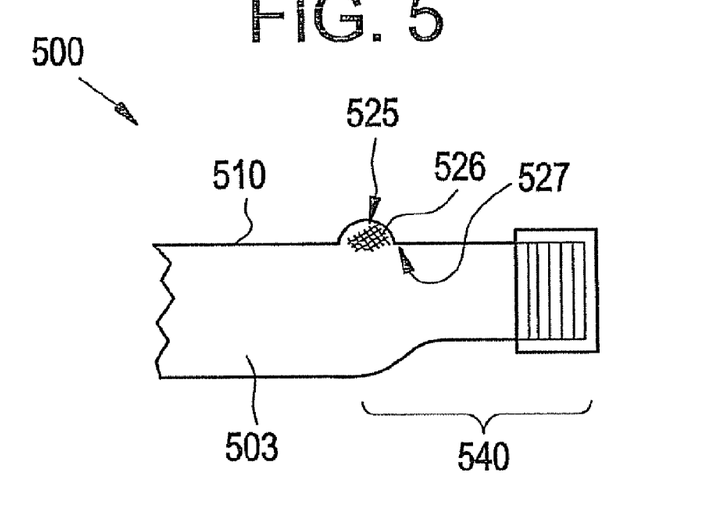
FIG. 5 is a partial cross-sectional side view of a further embodiment of the present invention.

A vessel 500 has an inverted construct 525 (FIG. 5) within an internal volume 503. The inverted construct 525 is an upturned U-shaped projection 525 in a top surface 510 and forms a gas collection area 526 in the internal volume 503. Advantageously, the inverted construct 525 can be molded integrally with the top plate 510. When the apparatus 500 is tilted from a vertical filling position to the horizontal growth position as illustrated, extraneous gas/bubbles are trapped in the gas collection area 526 where the gas/bubbles are isolated away from internal cell growth areas of the internal volume 503. Various modification of the gas collection area 526 in combination with a surface or wall 527 of the neck portion 540 can be incorporated in the vessel 500. Further, any size or shape of constructs 525 (e.g. U-shaped or V-shape, etc.) may facilitate trapping of the extraneous gas or bubbles.

Figure 6:
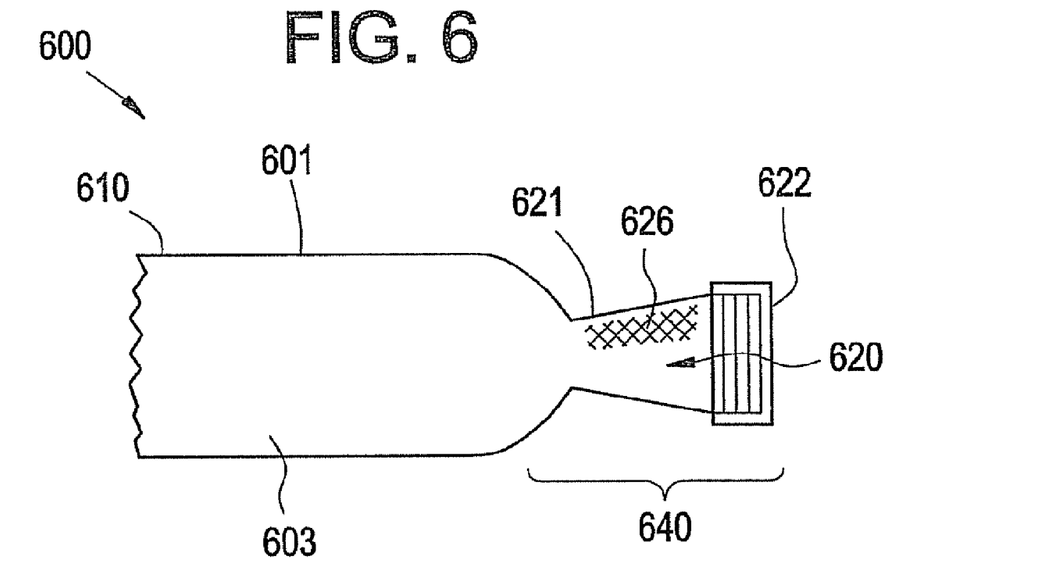
FIG. 6 is a partial cross-sectional side view of a further embodiment of the present invention.
Figure 7:
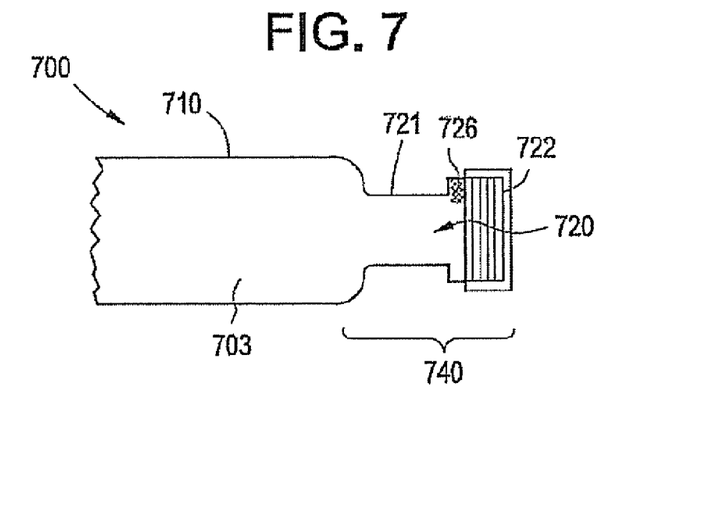
FIG. 7 is a partial cross-sectional side view of a further embodiment of the present invention.

As illustrated in FIGS. 6 & 7, a tapered or narrowed neck may trap extraneous gas or bubbles when the vessel is tilted from a vertical filling position to a horizontal growth position (with top plates 610/710 upright). A vessel 600 has a tapered neck portion 640 in which a narrowed neck 621 isolates a gas collection area 626 from an internal volume 603. An opening 620 in the tapered neck portion 640 remains accessible to the internal volume 603 by way of a removable cap 622. Another embodiment of the present invention is illustrated in a vessel 700. A narrowed neck 721 isolates a gas collection area 726 in a tapered neck portion 740. The narrowed neck 721 traps any gas or bubbles remaining in the vessel 700 when the vessel is tipped from a vertical filling position to a horizontal growth position (as shown) while still permitting access to the internal volume 703 through an opening 720 via a removable cap 722.

Figure 9:
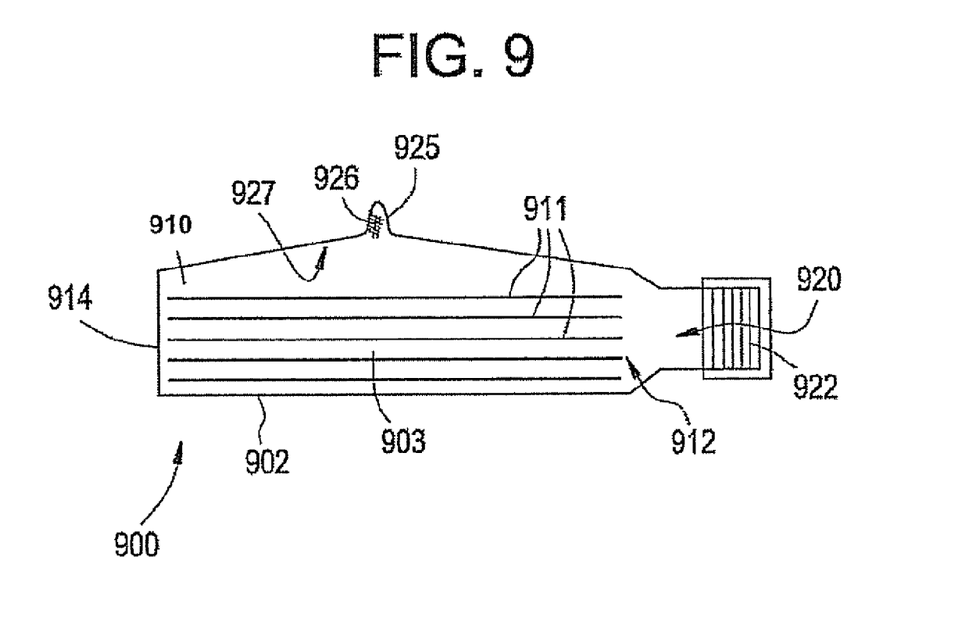
FIG. 9 is an external side view of a device in another embodiment of the present invention.

FIG. 9 describes another embodiment of the present invention. An internal volume 903 of a vessel 900 is defined by the top plate/surface 910, bottom tray 902, sidewalls 912, and endwalls 914. A recess 925 is integrally molded in a middle section of the top plate 910 so that a gas collection area 926 is formed in the top surface 910 (an upmost surface when the vessel 900 is positioned horizontally as shown) of the internal volume 903. Disposed within the vessel 900 are multiple layers 911 that support cell growth. As the vessel 900 is filled with cells and/or media in a vertical filling position (with an opening 920 facing upright), any air or bubbles in the internal volume 903 remain near the opening 920. When the vessel 900 is inclined from a vertical filling position with a cap 922 facing upright to a horizontal position (as shown in a perspective view of the vessel 900), extraneous gas or bubbles that remain in the internal volume 903 are confined in the gas collection area 926 of the top plate 910.

Figure 10:
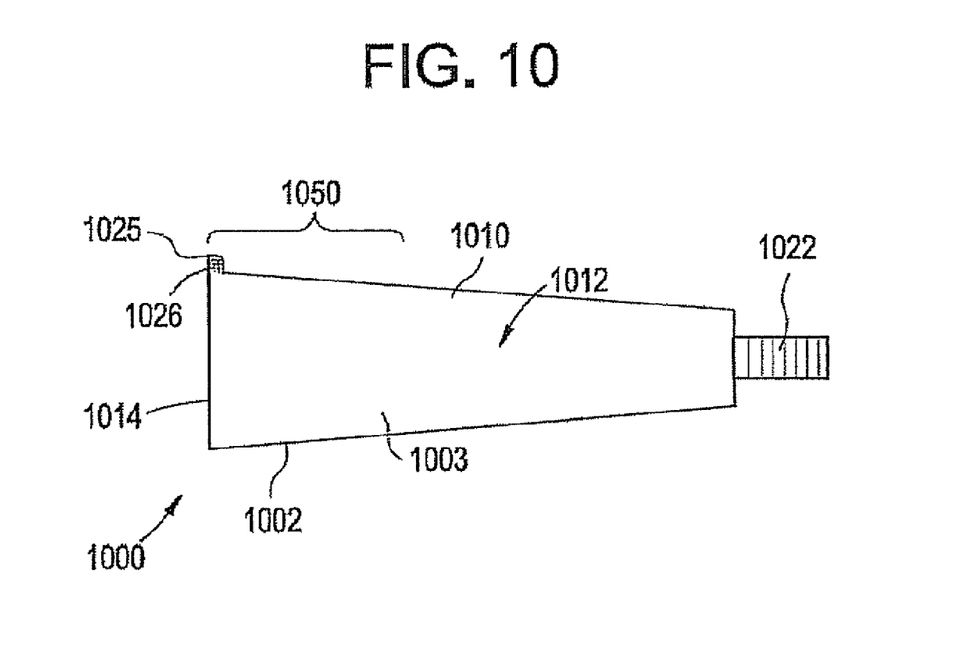
FIG. 10 is an external side view of a device in another embodiment of the present invention.

FIG. 10 also describes another embodiment of a vessel 1000 having a gas collection area 1026 within an internal volume 1003. An internal volume 1003 of a vessel 1000 is defined by a top plate 1010, a bottom tray 1002, sidewalls 1012, and endwalls 1014. The gas collection area 1026 is formed by a recess 1025 in a topmost section 1050 of the top plate 1010. When the vessel 1000 is filled with cells and/or media and then tilted from a vertical position with cap 1022 facing upright to a horizontal position with top plate 1010 facing upright (as illustrated), any gas or bubbles that remain in the internal volume 1003 migrate to the topmost section 1050 and get trapped in the gas collection area 1026.

As exemplified, various possible embodiments of the present invention offer several improvements over standard vessels currently used in industry. The improved cell culture devices enhance the growth of cells within cell culture chambers when media substantially fills the internal volume of a vessel by preventing undesired gaseous components from entering the cell growth areas. In addition, the embodiments of the present invention may be modified to take the shape of any device, container, apparatus, vessel, or flask currently used in industry. For example, cylindrical, spiracle, or alternatively shaped vessels may utilize a gas collection area to remove gas or bubbles from the cell culturing environment.

The apparatus may include any unitary structure, vessel, device or flask that would benefit from the capture and/or removal of gas from an internal volume. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

We claim:

1. A device for trapping extraneous gas or bubbles comprising:
   one or more surfaces defining an internal volume;
   at least one opening in said one or more surfaces; and
   a gas collection area incorporated within said internal volume;
     wherein said gas collection area is defined by a flange extending from said one or more surfaces within said internal volume,
   wherein the device comprises a cell growth chamber;
   whereby when said internal volume is substantially filled with a liquid and tilted, said gas collection area traps said extraneous gas.

2. The device according to claim 1, wherein said one or more surfaces include a top surface, a bottom surface, and sidewalls and/or end walls.

3. The device according to claim 1, wherein the one or more surfaces comprise a neck portion.

4. The device according to claim 3, wherein said gas collection area is included in the neck portion.

5. The device according to claim 4, wherein the gas collection area comprises an angled neck portion.

6. The device according to claim 4, wherein the neck comprises an angled neck.

7. The device according to claim 4, wherein the neck comprises a tapered neck.

8. The device according to claim 1, wherein said flange extends from a surface of a tapered neck portion.

9. The device according to claim 1, wherein said flange is positioned at an angle.

10. The device according to claim 8, wherein said flange comprises an annular circumferential flange.

11. A method of culturing cells comprising:
    providing a cell growth apparatus for trapping extraneous gas or bubbles comprising:
      one or more surfaces defining an internal volume; an opening in said one or more surfaces; and a gas collection area incorporated in said internal volume;
        wherein said gas collection area is defined by a flange extending from said one or more surfaces within said internal volume;

introducing cells and/or media into said cell growth apparatus in a vertical filling position,
filling said internal volume,
tilting said apparatus to a horizontal cell growth position,
allowing extraneous gas or bubbles to be captured in said gas collection area, and
incubating said apparatus.

12. The method according to claim 11, further comprising a step of removing said extraneous gas.

13. The method according to claim 11, further comprising a step of rotating said apparatus to culture cells on an opposing surface.

* * * * *